(12) United States Patent
Hansen

(10) Patent No.: US 8,263,413 B1
(45) Date of Patent: Sep. 11, 2012

(54) METHODS FOR ANALYZING LIPIDS AND MEMBRANE PROTEINS IN BIOLOGICAL MATTER USING STABLE ISOTOPES AND MASS SPECTROMETRY

(76) Inventor: Andrew S Hansen, Bountiful, UT (US)

( * ) Notice: Subject to any disclaimer, the term of this patent is extended or adjusted under 35 U.S.C. 154(b) by 461 days.

(21) Appl. No.: 12/581,023

(22) Filed: Oct. 16, 2009

Related U.S. Application Data

(60) Provisional application No. 61/106,443, filed on Oct. 17, 2008.

(51) Int. Cl.
*G01N 24/00* (2006.01)
*G01N 33/92* (2006.01)
*G01N 33/53* (2006.01)

(52) U.S. Cl. ............... 436/173; 436/13; 436/71; 435/7.2

(58) Field of Classification Search .................. 436/173, 436/13, 71; 435/7.2
See application file for complete search history.

(56) References Cited

U.S. PATENT DOCUMENTS

| | | | |
|---|---|---|---|
| 4,446,237 A | 5/1984 | Berninger | |
| 4,977,320 A | 12/1990 | Chowdhury et al. | |
| 5,045,694 A | 9/1991 | Beavis et al. | |
| 5,245,186 A | 9/1993 | Chait et al. | |
| 5,338,686 A | 8/1994 | Hellerstein | |
| 5,366,721 A | 11/1994 | Turteltaub et al. | |
| 5,376,355 A | 12/1994 | Turteltaub et al. | |
| 5,453,247 A | 9/1995 | Beavis et al. | |
| 5,572,024 A | 11/1996 | Gray et al. | |
| 5,800,979 A | 9/1998 | Kolhouse et al. | |
| 6,391,649 B1 | 5/2002 | Chait et al. | |
| 6,642,059 B2 | 11/2003 | Chait et al. | |
| 6,653,076 B1 * | 11/2003 | Franza et al. | ................ 435/6.16 |

OTHER PUBLICATIONS

Bijlsma et al, "Large-scale human metabolomics studies: A strategy for data(pre-) processing and validation" Anal Chem 2006, 78:567-574.
Boone et al, "Isolation of Plasma Membrane Fragments from HELA cells", J. Cell Biol. vol. 41 p. 378, 1969.
Coxx et al., "Is Proteomics the new Genomics?", Cell, vol. 130, Issue 3, pp. 395-398, 2007.
Ekroos et al, "Quantitative profiling of phospholipids by multiple precursor ion scanning on a hybrid quadruple time-of-flight mass spectrometer", Anal Chem 2002, 74:941-9949.
Gerrit Van Meer, et al, "Membrane lipids: where they are and how they behave", Nature Reviews Molecular Cell Biology 9, 112-124 (Feb. 2008) | doi:10.1038/nrm2330.
Guan et al., "Non-Targeted profiling of lipids during kainite-induced neutronal injury", The FASEB Journal, Research Communication, vol. 20, Jun. 2006, pp. 1152-1161.
Han et al, "Global Analyses of cellular lipidomes directly from crude extracts of biological samples by ESI mass spectrometry: a bridge to lipidomics", J Lipid Res 2003, 44:1071-1079.
Han et al, "Shotgun Lipidomics: Electrospray Ionization Mass Sectrometric Analysis and Qunatiation of Celullar Lipidomes Directly from Crude Extracts of Biological Samples", Mass Spectrometry Reviews, Jun. 18, 2004.

(Continued)

*Primary Examiner* — Rosanne Kosson

(57) ABSTRACT

Methods for accurately comparing the levels of ionizable lipids in two cell populations that differ in some respect from each other using mass spectroscopy and isotopic labeling are provided. The methods can be used to identify a change in a lipid of interest in response to a cellular, chemical, genetic, or environmental change to the cell population (i.e., a lipid response to a cell perturbation). The change in the lipid of interest can be a change in composition, rate of synthesis, and/or location of the lipid.

12 Claims, 2 Drawing Sheets

OTHER PUBLICATIONS

Hermanson et al, "Automated quantitative analysis of complex, lipidomes by liquid chromatography/mass spectrometry", Anal Chem 2005, 77:2166-2175.

Houju et al, "A shotgun tandem mass spectrometric analysis of phospholipids with normal-phase and/or reverse-phase liquid chromatography/electrospray ionization mass", Rapid Comm Mass Spectrom 2005, 19:654-666.

Ivanova et al, "Lipidomics: a mass spectromtry based systems levela analysis of cellular lipids", Current Opinion in Chemical Biology 2009, vol. 13, pp. 526-533, Sep. 8, 2009.

Kainu et al, "Electrospray Ionization Mass Spectrometry and Exogenous Heavy Isotope-labeled Lipid Species Provide Detailed Information on Aminophospholipid Acyl Chain Remodeling", Journal of Biological Chemistry, vol. 283, No. 6, Feb. 8, 2008.

Kayganich-Harrison, Kathleen A., et al., "Incorporation of stable isotope-labeled arachidonic acid into cellular phospholipid molecular species and analysis by fast atom bombardment tandem mass spectrometry", Biological Mass Spectrometry, vol. 23, Issue 9, pp. 562-571, 1994.

Ogiso et al., "Development of a reverse-phase liquid chromatography electrospray ionization mass spectrometry method for lipidomics, improving detection of phosphatidic acid and phosphatidylserine", Analytical Biochemistry. vol. 375 (2008) pp. 124-131, doi:10.1016/j.ab.2007.12.027.

Wenk, Markus R.,"The Emerging Field of Lipidomics" Nature Reviews, Drug Discovery, vol. 4, Jul. 2005 pp. 594-610.

\* cited by examiner

METHODS FOR ANALYZING LIPIDS AND MEMBRANE PROTEINS IN BIOLOGICAL MATTER USING STABLE ISOTOPES AND MASS SPECTROMETRY

CROSS-REFERENCE TO RELATED APPLICATIONS

This application claims the benefit of U.S. Provisional Application No. 61/106,443, filed Oct. 17, 2008, and entitled "METHODS FOR ANALYZING LIPIDS AND MEMBRANE PROTEINS IN BIOLOGICAL MATTER USING STABLE ISOTOPES AND MASS SPECTROMETRY", the disclosure of which is hereby incorporated herein by reference in its entirety.

FIELD OF THE INVENTION

The invention relates to analyzing lipids in biological matter to identify or quantify differences in two samples of a cell population, one of which has been subjected to cellular, environmental, genetic, or chemical modulation.

BACKGROUND INFORMATION

A biological membrane (biomembrane) is an enclosing, or separating amphipathic layer, which acts as a barrier within or around a cell. A biomembrane is usually a lipid bilayer composed of a double layer of lipid-class molecules with proteins intertwined.

Biomembranes typically define enclosed spaces or compartments in which cells maintain a chemical or biochemical environment that differs from the outside. One important feature of biomembranes is that they are selectively permeable structures. The size, charge, and other chemical properties of the molecules that make up the biomembrane determine whether other molecules can pass through the biomembrane. Biological membranes also have certain mechanical or elastic properties.

The selective permeability and mechanical or elastic properties of the cell are determined by the type of lipids and proteins that make up the biomembrane. There are three classes of lipids that are commonly found in biomembranes: phospholipids, glycolipids, and cholesterols. The relative composition of each of these lipids in any given biomembrane depends on the type of cell and other biological factors. A cell membrane, for example, can have thousands of different lipids, some of which may be in high concentration and some of which may be in very low concentrations. Moreover, the lipid composition of biomembranes can change in subtle ways in response to cellular, genetic, chemical, or environmental changes.

Biomembranes such as the cell membrane also include a large amount of protein that gives the cell important characteristics. The amount of membrane protein differs between species and according to function, however the typical amount of protein in a cell membrane is 50%. A membrane protein can be any protein molecule that is attached to, or associated with the membrane of a cell or an organelle. Membrane proteins can be classified into different groups based on the strength of their association with the membrane. An important class of membranes that is highly associated with the membrane is integral membrane proteins, which includes transmembrane proteins.

Biomembranes, including those having integral membrane proteins, are notoriously difficult to study. Often, the amphipathic nature of the membrane proteins makes it difficult to study these proteins in solution. Extracting membrane proteins from the membrane often results in agglomeration, denaturing, and/or deactivation of the membrane proteins. Consequently, membrane proteins are often studied while in the membrane. However, studies of whole membranes are difficult because of the numerous lipids and proteins that are present in biomembranes.

SUMMARY OF THE INVENTION

Disclosed are methods for accurately comparing the levels of ionizable lipids in two cell populations that differ in some respect from each other using mass spectroscopy and isotopic labeling. The methods can be used to identify a change in a lipid of interest in response to a cellular, chemical, genetic, or environmental change to the cell population (i.e., a lipid response to a cell perturbation). The change in the lipid of interest can be a change in composition, rate of synthesis, and/or location of the lipid. In one embodiment of the invention, the method can be used to identify lipids that are associated with a membrane protein by modulating the membrane protein (e.g., over-expressing the protein) and identifying a corresponding change in the composition and/or concentration of the lipid of interest.

One embodiment of the present invention relates to a method for comparing the relative abundance of a lipid of interest in multiple samples of a cell population. The method employs at least two samples of a cell population, one of which has lipids that are isotopically labeled. The use of two samples, one of which has isotopically labeled lipids, allows the lipids in the samples to be combined for processing purposes, yet remain distinguishable in a mass spectrometer. In one embodiment the isotopic labeling is carried out by using an isotopically labeled lipid precursor in the media used to culture the cell population. The cells in the labeled sample are allowed to divide and/or grow in the media for a sufficient time to ensure incorporation of the isotopically labeled lipid precursors into the cells of the sample.

The lipid precursor can be selected to achieve labeling of a desired type of lipid and/or to select the extent of the isotopic labeling. Examples of suitable lipid precursors that can be isotopically labeled include glucose, glycerol, cholesterol, and/or serine. Labeled glucose can be used to label the long-chain hydrocarbons of lipids and can therefore be used to label essentially all lipids. Other lipid precursors can be used to specifically label certain kinds of lipids. For example, glycerol can be used to label glycolipids; labeled cholesterol can be used to label cholesterol and its derivatives; and labeled serine can be used to label sphingolipids.

To carry out the isotopic labeling of the samples, a first sample of the cell population is cultured in a first medium including one or more lipid precursors having a first abundance of isotopes (e.g., a natural abundance). A second sample of the cell population is cultured in a second medium containing the lipids precursors having more or less than the first abundance of the one or more isotopes. One of the samples is modulated and at least a portion of each sample of the cell population is combined to form a combined sample.

Prior to or after combining the lipids to form a combined sample, at least one lipid of interest from each sample is isolated. Any technique compatible with preparing a sample for mass spectrometry can be used to isolate the lipids from the first and second sample and/or the combined sample. While the technique can be carried out by isolating a single lipid, in many cases, two or more lipids are isolated and in some cases, tens, hundreds, or even thousands of lipids can be isolated and used in the mass spectrometry step.

The lipids can be isolated as an insoluble lipid, a soluble lipid, or a lipid suspension. Insoluble lipids include, but are not limited to lipid membranes (e.g. a fully intact or partially intact biomembrane). Other examples of insoluble lipids include lipid composites such as, but not limited to polymer films. Soluble lipids include lipids that have been extracted into an organic solvent or extracted using a detergent. Lipid suspension include lipid vesicles and lipid bilayers. Examples of solubilizing reagents include poly(lactide-co-glycolide) PLGs, PEGs and PEGylation.

In one embodiment, the lipids are isolated by lysing the cells of the sample and extracting the membrane fraction of the cell lysate. For example, the cells of the sample or samples can be lysed and centrifuged and the membrane fraction collected and re-suspended in a buffer solution. Isolation of the lipids or membranes from the sample can be carried out using any technique that separates lipids or membranes from other components of the sample. Examples of other suitable extraction and/or separation techniques include, but are not limited to cell lysis, low speed centrifugation, high speed centrifugation, ultra centrifugation, density gradient centrifugation, lipid extraction, high performance liquid chromatography, ultra pure liquid chromatography, electrophoresis (including but not limited to capillary electrophoresis), affinity chromatography, and other separation techniques known in the art. Examples of suitable affinity chromatography techniques include immobilizing a protein that binds a lipid (e.g., a lipoprotein such as but not limited to LDL and/or HDL) or an antibody with specificity for a lipid.

Optionally, the isolated lipids or membranes can be further purified or/or separated into one or more desired fractions. The purification and/or separation step, can include separating biomembranes from biomembranes (e.g., biomembrane from endoplasmic reticulum, separating membranes or lipids from organelle (e.g., mitochondria), separating a hydrophilic fraction from a hydrophobic fraction, separating one type of lipid from another type of lipid, separating lipids from protein, separating lipids from nucleic acids, or a combination of these.

The isolated lipid or lipids are then subjected to mass spectroscopy to develop a mass spectrum. The difference in the mass of the lipid precursor in each cell population results in two distinct, closely spaced peaks in the mass spectrum (i.e., a peak pair). One peak of the peak pair corresponds to a lipid from the cell population that includes the lipid precursor having the first abundance of isotopes (e.g., a natural abundance). The other peak corresponds to a lipid from the cell population that includes a lipid precursor enriched or depleted in one or more isotopes compared to the first abundance.

To determine a change in the lipid of interest, the ratio of one or more peak pairs in the mass spectrum is computed. The relative abundance of the lipid in each cell population or a fraction of the cell population (e.g., a biomembrane) can be determined based on the computed ratio. The lipid of interest may be identified by the mass-to-charge ratios of the peaks in the mass spectrum, as well as by other means known in the art of mass spectrometry.

The mass spectrometry can be highly sensitive to small changes in a lipid of interest. The change in the lipid of interest can then be associated with the difference in the perturbed sample as compared to the other sample.

The change in the lipid can be the presence or absence of lipid, a change in the location of the lipid within the cell or within the cell population, and/or the molecular modification of the lipid (e.g. phosphorylation, glycosylation, dehydrogenation, etc.), or a combination of these.

In an alternative embodiment of the invention, a biological component, such as but not limited to, lipid, protein, nucleic acid, hormone, small organic molecule, cofactor and/or carbohydrate can be associated with a membrane protein. In this embodiment, two samples of a cell population are grown as described above and a biological component (e.g., lipid, protein, and/or carbohydrate) of the samples is isotopically labeled (e.g., by incorporating labeled and unlabeled biological component precursors into the respective samples). Then, one of the two cell populations is perturbed by modulating a membrane protein. The modulation of the membrane protein can be, for example, over expression of the membrane protein or a chemical modification of the membrane protein. The modulation of the membrane protein also causes a difference in the biological component in that sample. Then, a portion of each sample is combined and the biological component is isolated and subjected to mass spectrometry. The relative abundance of the biological components from one sample of the cell population are compared with the relative abundance of the same biological components in the second sample of the cell population and lipids that had a significant increase or decrease in the perturbed cell population are identified.

In one embodiment of the invention the biological component is isolated from the samples with a biomembrane (the target biomembrane). In this embodiment, isolating different types of biomembranes can be advantageous for identifying biological components that are associated with a particular integral membrane protein. In some cases, it may be the case that the change in the biological component is only a local change. For example, the concentration of a lipid or protein in the biomembrane may go up or down while the overall concentration of the biological component in the cell or cytosol does not change, such as when the biological component is simply transported from another location in the cell and attached to or inserted into the biomembrane. Isolating certain types of biomembranes (i.e., the target biomembrane) from other biomembranes can identify changes in the biological component within the target biomembrane even if there is no net change in the overall sample and/or the change in the overall sample is undetectable.

These and other features of the present invention will become more fully apparent from the following description and appended claims.

The present invention is directed to a method for accurately comparing the levels of ionizable lipids in two cell populations that differ in some respect from each other, using mass spectroscopy and isotopic labeling. The method can be used to identify a change in a lipid of interest in response to a cellular, chemical, genetic, or environmental change to the cell population. The change in the lipid of interest can be a change in composition, rate of synthesis, and/or location of the lipid within a biomembrane, cell, or tissue.

In another embodiment of the invention, the method can be used to identify a biological component (such as, but not limited to, lipids) that are associated with a membrane protein by modulating the membrane protein (e.g., modulating expression) and identifying a correlative change in the composition and/or concentration of the biological component of interest.

Figure 1:
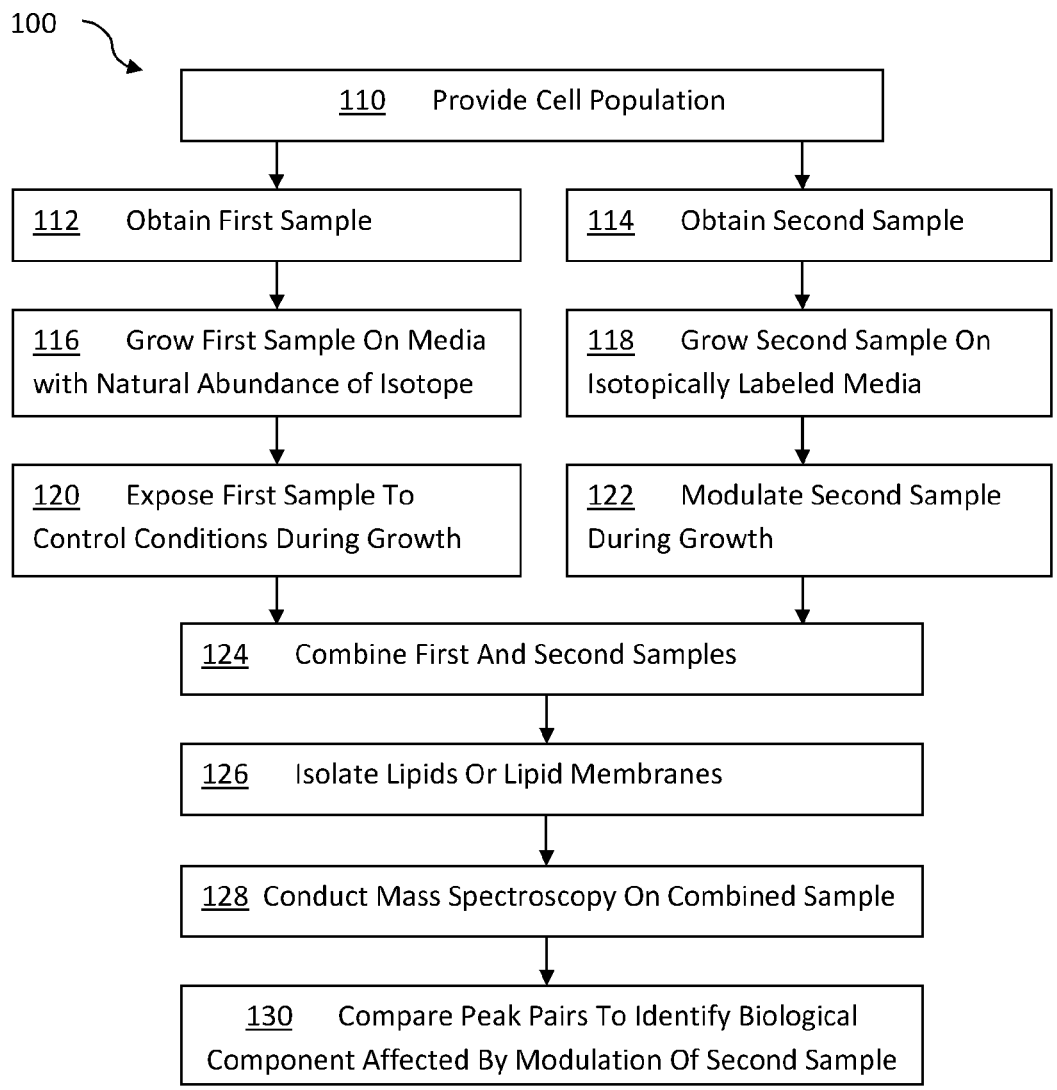
FIG. 1 is a flow chart describing a method for identifying for analyzing lipids in biological matter using stable isotopes.

FIG. 1 illustrates a general flow diagram 100 for carrying out a method according to one embodiment of the invention. As shown in FIG. 1, in step 110 a cell population is provided. The cell population can be any type of cell or biological matter capable of replicating, including individual cells, tissues, organs, organisms, or a cell mimetic. In steps 112 and 114, respectively, a first sample and a second sample are taken from the cell population. In step 116 the cells from sample 1 are grown on a media with a normal abundance of isotopes. The cells are maintained in a growth phase, thereby incorporating the natural abundance of isotopes into the cells of the first sample. Similarly, in step 118, the second sample is grown on a media. However, the media for sample 2 includes lipid precursors that differ in the concentration of isotope from the media used to grow the first sample. For purposes of this invention, lipids and lipid precursors that have an abundance of one or more isotopes that is different than a natural abundance of isotopes is an "isotopically labeled" lipid or lipid precursor. Those skilled in the art will recognize that the first sample and second sample can both be isotopically labeled so long as the isotopic labeling differs in some respect between the two samples. If desired, one sample can incorporate a lipid precursor with a natural abundance of isotope and the other sample can incorporate a precursor that is isotopically labeled.

In steps 120 and 122, the first sample is exposed to control conditions and the second sample is modulated to cause a particular change in the cells of the sample. Once the desired change occurs in the second sample, the samples are combined (step 124) to form a combined sample. Thus, the combined sample includes lipids from the first sample that are the same as lipids from the second sample, except that the lipids from the second sample are isotopically labeled.

In step 126, a portion of lipids are isolated and prepared for mass spectrometry and in step 128 the lipids are subjected to mass spectrometry. While it is preferred to carry out step 126 after forming a combined sample to avoid variation in the samples, the present invention can also be carried out where the first and second samples are combined after performing one or more separation techniques as described below. The mass spectrometry data is then used in step 130 to compare the abundance of lipids in the first sample compared to the second sample to identify changes in the lipids or other biological component of the second sample that are attributable to the modulation.

Isotopically Labeling Lipids in a Sample of a Cell Population

To identify a change in lipids in one sample of a cell population compared to a another sample, one of the two samples is cultured in a media that contains isotopically labeled lipid precursors. The lipid precursors are selected to ensure labeling of certain lipids, or alternatively all lipids in the cells, and the media is selected to be compatible with the lipid precursors.

A. Sample of a Cell Population

The samples of the cell population are taken from a cell culture or other biological matter capable of replicating. The cell population can be individual cells, tissues, organs, organisms, or a cell mimetic. The samples can be taken from a single cell culture or from two or more cell cultures of the same general type of cells (e.g., cells from the same cell line). The pertinent factor in selecting samples of a cell population is that the two samples have a similar composition and behave similarly in similar conditions.

If a cell culture is used, the cell culture is typically provided in a cell media. Any cell media compatible with the cell population can be used in the present invention (e.g., Dulbecco Modified Eagle Medium "DMEM"). The cell media can be used to facilitate isotopic labeling of one of the samples. For example, the cell media can include labeled lipid precursors that are then incorporated into the lipids of the sample, as described below.

B. Isotopically Labeled Lipids and Lipid Precursors

The methods of the invention include incorporating an isotopically labeled lipid precursor into one or more of the samples of the cell population. Mass isotopically labeled components can be distinguished from naturally occurring, non-labeled components, by being one mass unit heavier. The stable isotopes of common elements useful in the methods of the present invention include, but are not limited to, carbon ($^{13}C$), hydrogen ($^{2}H$), oxygen ($^{18}O$), and nitrogen ($^{15}N$). These stable isotopes are available commercially as elements or in some lipid precursors or can be incorporated into the lipids or lipid precursors as discussed more fully below. In the practice of the present invention it is preferred that the labeled element or component be stable, and that any preparation containing the labeled component be at least more than about 85%, typically more than 95%, and preferably more than about 98% enriched with the stable isotope or isotopes. A high level of enrichment is preferred to ensure that the majority of the lipid precursors incorporated into newly synthesized lipids will be labeled.

The lipid precursor can be any component of the sample that is used by the cell to make a membrane or carry out a lipid facilitated process. Typically, the more basic the lipid precursor is in the catabolism of biological lipids, the more likely that the lipid precursor will effectively label multiple different types of biological lipids. If isotopic labeling of only a few particular lipids is desired, components further along in the catabolic process can be used. In some embodiments the lipid precursor may be non-specific and label all components of a cell, in addition to lipids.

One very rudimentary lipid precursor that can be used in the present invention is isotopically labeled glucose. Essentially all biological lipids can be isotopically labeled by growing a sample of a cell population on an isotopically labeled glucose source. This approach can be advantageous to ensure widespread labeling of biological lipids in the sample. The use of glucose to isotopically label lipids also has the advantage of labeling other components of the cell, such as proteins and carbohydrates.

In some cases it can be desirable to label the biological lipids using a component of the headgroup or "backbone" of the lipid. Labeling a headgroup type molecule can be effective for isotopically labeling because it reduces the number of isotopes per lipid molecule. Examples of particularly useful isotopically labeled head group molecules that can be used in the method of the present invention include glycerol and serine. Glycerol can be isotopically labeled at one or more of its carbons (e.g., with $^{13}C$) and/or alternatively at one or more of its oxygens (e.g., with $^{18}O$). Isotopically labeled glucose, serine, and glycerol are commercially available from Cambridge Isotope Laboratories (Andover, Mass.).

All cells have proteins and carbon sources that enable a cell to make the specific lipids needed for cell growth and function. Most, but not all lipids, fall within three general types of lipids made in most cells: phospholipids, glycolipids, and cholesterols.

Phospholipids include two subclasses of lipids: phosphoglycerides and sphingomyelin. In cell membranes (also referred to as the plasma membrane), phosphoglycerides are the more common of the two phospholipids. In phosphoglycerides, the carboxyl group of each fatty acid is esterified to the hydroxyl groups on carbon-1 and carbon-2 of the glycerol molecule. The phosphate group is attached to carbon-3 by an ester link. This molecule, known as a phosphatidate, is present in small quantities in membranes, but is also a precursor for the other phosphoglycerides.

The backbone of sphingomyelin is sphingosine, an amino alcohol formed from palmitate and serine. The amino terminal is acylated with a long-chain acyl CoA to yield ceramide. Subsequent substitution of the terminal hydroxyl group by phosphatidyl choline forms sphingomyelin. Sphingomyelin is also present in all eukaryotic cell membranes, especially the plasma membrane, and is particularly concentrated in the nervous system because sphingomyelin is a major component of myelin, the fatty insulation wrapped around nerve cells by Schwann cells or oligodendrocytes. Sphingomyelin can be isotopically labeled using an isotopically labeled serine or glucose, and/or phosphatidyl choline.

Cholesterol is a lipid found in the cell membranes of all tissues, and it is transported in the blood plasma of all animals. Cholesterol plays a central role in many biochemical processes, such as the composition of cell membranes and the synthesis of steroid hormones. Cholesterol is insoluble in blood, so its transport in aqueous environments is carried out by binding the cholesterol to one or more lipoproteins such as low-density lipoprotein (LDL) or high-density lipoprotein (HDL). These proteins are spherical particles which have an exterior composed mainly of water-soluble proteins.

Since cholesterol is typically made in the cell from glucose, cholesterol can be effectively labeled using $^{13}C$ labeled glucose. Alternatively, the lipid precursor for cholesterol type molecules can be a sterol. The sterol can include isotopically labeled carbons or an isotopically labeled oxygen on the alcohol of the sterol.

For purposes of this invention, a "lipid precursor" can be any part of biological lipid. In some cases, the lipid precursor need not be covalently modified for its incorporation into the cell population. For example, the precursor for cholesterol may be cholesterol or a lipoprotein bound cholesterol that is subsequently incorporated into a cell cell.

C. Incorporation of Lipid Precursor

The lipid precursor is incorporated into biological lipids by allowing the cells of the sample to multiply on the media. The cells in the sample uptake the lipid precursor from the cell media and incorporate the lipid precursor into the cellular system. In the sample that includes a non-natural abundance of isotope, each cell division results in a larger percentage of the cell population having lipids labeled with the non-natural abundance of isotope.

In a preferred embodiment, the lipid is fully incorporated into the sample. Full incorporation can be achieved by allowing the population of cells to double at least about 5, more preferably at least 10, and most preferably at least about 20 times. It can be advantageous to ensure that the isotope is fully incorporated into the lipids of the sample to obtain a higher degree of sensitivity for detecting changes in the lipid concentration. Fully incorporating the isotope is advantageous in the present invention because the lipids are generally small molecules (as compared to DNA and many polypeptides) and fully incorporating the isotope allows the technique to be more sensitive to changes in the lipid (e.g., changes in concentration). However, if desired, the present invention can be carried out on samples where the incorporation of the lipid is not complete. In this embodiment, multiple samples can be taken at different periods of the cell growth and the change in a lipid of interest over time can be investigated. Additional details regarding the incorporation of an isotopically labeled precursor into a sample of a cell over a period of time are disclosed in U.S. Pat. No. 6,653,076 Franza, which is hereby incorporated herein by reference.

In a preferred embodiment, the isotopic labeling of the sample with the non-natural abundance of isotope is facilitated by providing the media with a depletion of the lipid precursor having a natural abundance of isotope. For example, if the lipid precursor is a labeled glucose, the media for the sample to be labeled is provided with a depletion in glucose having a natural abundance of isotope.

To ensure that the labeled lipid precursor is incorporated into the cells of the labeled sample, the cells can be manipulated to prevent the conversion of non-labeled cellular components into the lipids intended to be isotopically labeled. For example, where a labeled glycerol is used as a lipid precursor, the cellular mechanisms for converting glucose to glycerol can be inhibited or blocked. To block conversion of glucose to glycerol, the enzymatic reactions for this conversion can be inhibited using genetic engineering to delete the enzymes that catalyze the conversion or suppression techniques such as siRNAs can be used.

Modulating a Sample of the Cell Population

The purpose of modulating one of the samples of the cell population is to create a biological difference of interest between the one or more samples of the cell population. The modulation is selected to create a difference in the one or more samples that can be identified by detecting a change in the lipids of the cell population. A sample can be modulated using any technique that can affect a lipid or other biological component that is associated with a lipid of a cell population. Examples of suitable modulations that can be carried out on a sample of a cell population include, but are not limited to, cellular, chemical, genetic, and/or environmental changes.

Where the modulation includes a chemical change, the chemical change can be any chemical that produces a desired effect of interest. Examples of suitable chemical changes include exposing the sample of the cell population to an acid or a base to adjust the pH (acidic, neutral, or basic); exposing the sample to a small molecule, such as a drug or toxin; changing the ion concentration of the cell media or adding particular types of ions; modifying cell permeability (e.g., using an ionophore) and/or exposing the sample to a hormone or other biological chemical.

Where the modulation includes a genetic change, the sample can be modified by upregulating or down regulating a gene. The gene regulation can be carried out using any known techniques for regulating gene expression in a cell population. For example, in one embodiment, the modulation can be carried out by over-expressing a particular protein in the sample using a gene expression system. In an alternative embodiment, the genetic modulation can include a change in the transcription of mRNA in the sample using interfering RNA, including siRNA, miRNA, and/or piRNA. The genetic modulation can also be carried out by exposing the sample to a disease causing agent that causes a genetic alteration in the sample (e.g., exposure to a virus).

The modulation can also cause a cellular change. Examples of cellular changes include desensitization of an electrically excitable cell due to depolarization or localization of a kinase to the plasma membrane.

Where the modulation is an environmental change, the sample can be exposed to any environment that is different from another sample. Examples of suitable environmental differences include differences in temperature, pressure, electric potential, reducing environment, oxidizing environment, and/or the amount or type of radiation (e.g., UV radiation) exposed to a particular sample.

The modulated sample is allowed to grow under the modulated conditions for a sufficient amount of time to ensure that the change in the lipid occurs. The modulation changes at least one aspect of an ionizable lipid of the cell population. The change in the ionizable lipid can be a change in the ionizable lipid itself or alternatively a change in a biological component of the cell population that is associated with the ionizable lipid. The change in the lipid can be a change in the rate of synthesis, a change in the concentration of the lipid, and/or a chemical modification of the lipid, such as but not limited to, phosphorylation or glycosylation or any other change that results in the lipid having a different mass or different concentration in the modulated sample compared to the other sample (i.e., the control sample).

If desired, more than one different type of sample modulation can be simultaneously analyzed. To simultaneously analyze two or more sample modulations additional samples with media containing a different isotope with a different abundance than the abundance of the isotope in the first and second samples. Preparing a sample with a third abundance of isotope allows the lipids from the third sample to be distinguished from the first and second samples. Any number of distinct samples can be prepared so long as a signature isotope can be incorporated into the sample.

Sample Preparation

After modulating one of the samples, the lipids are isolated and prepared for mass spectrometry. The lipids can be isolated as an insoluble lipid, a soluble lipid, or a lipid suspension. Insoluble lipids include, but are not limited to lipid membranes (e.g. a fully intact or partially intact biomembrane). Other examples of insoluble lipids include lipid composites such as, but not limited to polymer films. Soluble lipids include lipids that have been extracted into an organic solvent or extracted using a detergent. Lipid suspension include lipid vesicles and lipid bilayers. Examples of solubilizing reagents include poly(lactide-co-glycolide) PLGs, PEGs and PEGylation.

The lipids or membranes can be isolated by extracting, purifying, and/or separating the lipids in any number of steps and/or using any technique, so long as the isolation technique is compatible with preparing a sample for mass spectrometry. Examples of suitable extraction and/or separation techniques include, but are not limited to cell lysis, low speed centrifugation, high speed centrifugation, ultra centrifugation, density gradient centrifugation, lipid extraction, high performance liquid chromatography, ultra pure liquid chromatography, electrophoresis (including but not limited to capillary electrophoresis), affinity chromatography, and other separation techniques known in the art. The particular isolation technique that is used will depend on the type of sample (e.g., cells, tissue, etc.) and/or the location of the lipids within the sample, the particular mass spectrometry equipment to be used for mass spec, and/or the number of different types of lipids that are to be purified.

The lipids are typically isolated into one or more desired fractions. The isolation can include separating biomembranes from biomembranes (e.g., biomembrane from endoplasmic reticulum, separating membranes or lipids from organelle (e.g., mitochondria), separating a hydrophilic fraction from a hydrophobic fraction, separating one type of lipid from another type of lipid, separating lipids from protein, separating lipids from nucleic acids, or a combination of these.

Typically lipid isolation includes centrifuging the sample to remove all or a portion of the aqueous fraction of the sample and lysing cells of the samples to facilitate separation of the lipids from the cytosol. An example of a suitable lysis solution is RIPA lysis buffer (available from Thermo Scientific). Following lysis and centrifugation, the lipids are typically re-suspended in a suitable buffer solution (e.g., tris-magnesium-sucrose).

In one embodiment, the lipid purification can include separating particular biomembranes and/or cell organelle from one another. Examples of types of biomembranes and/or cell organelle that can be separated from one another include, but are not limited to, cell membrane, nuclear envelope, mitochondria, endoplasmic reticulum, golgi body, etc. Reagents and protocol that can be used to isolate the cell membrane, nuclear envelope, endoplasmic reticulum, mitocondria are known. For example, the article Boone et al, titled "Isolation of Plasma Membrane Fragments From HELA Cells" (J. Cell Biol. Vol. 41 p. 378, 1969) describes a method for isolating the plasma membrane. The foregoing Boone article is hereby incorporated herein by reference).

Separating biomembranes of different types allows detection of lipids that have been moved from one type of biomembrane to another in response to the perturbation. This technique can be particularly advantageous for sample modulations (i.e., perturbations) where new lipids are not formed during the sample modulation but instead where the lipid or biological component is simply moved from one component (e.g., organelle) of the cell to another or from one region of an organism to another.

The sample can also be prepared by purifying labeled lipids of interest. The lipids can be extracted from a membrane using known techniques, such as but not limited to, solvent extraction techniques and chromatography techniques. An example of a suitable solvent extraction technique includes chloroform extraction. Examples of chromatography techniques that can be used include, but are not limited to liquid chromatography (e.g., HPLC or UPLC) or affinity chromatography.

The foregoing purification and/or separation steps can be performed separately or in combination. In some embodiments, the purification or separation techniques can be performed simultaneously with the initial isolation of the lipids. Because the present invention provides for isolation of lipids, in one embodiment, it can be advantageous to avoid a tryptic digest of the sample and/or avoid gel electrophoresis.

Prior to conducting mass spectrometry on the samples, the cells or the lipids from the samples are combined. In a preferred embodiment, the whole cells are combined prior to performing any extraction or purification to minimize differences in the lipid concentration between labeled and unlabled samples (i.e., difference that are associated with separation, not modification of the membrane protein). However, as those skilled in the art will appreciate, the samples can be combined at any point prior to mass spectrometry.

Up to the point of the mass spectroscopy, none of the steps of the process discriminates between a lipid that contains the first abundance of isotopes from the same lipid in the isotopically enriched or depleted cell population. Thus, the ratios of the original amounts of lipids from the two samples are maintained, thereby normalizing for differences between extraction and separation of the lipids in the cell populations. Optionally the concentration of one or more lipids or proteins in the first and second samples can be quantified and the first and second samples can be combined in desired concentration ratios of the lipid or protein (e.g., a 50:50 ratio of a protein from the first and second samples). Normalizing the concentration, while not necessary, can reduce background noise from the mass spectrometry data.

Mass Spectrometry

Once the samples are combined, mass spectrometry is carried out on the combined sample. Any mass spectrometer may be used to analyze the peptides or proteins so long as the peaks that identify the isotopically labeled lipids can be detected. For example, the mass spectrometer may be a Matrix-Assisted Laser Desorption/Ionization ("MALDI") Time-of-Flight ("TOF") Mass Spectrometer, available from PerSeptive Biosystems, Framingham, Mass.; an Electrospray Ionization ("ESI") ion trap mass spectrometer, available from Finnigan MAT, San Jose, Calif.; or an ESI quadrupole mass spectrometer, available from Finnigan MAT or the Perkin-Elmer Corporation, Foster City, Calif.

In one embodiment, the mass spectrometry may be carried out at least in part using shotgun lipidomics. Methods for performing shotgun lipidomics are described in more detail in the article titled, "Shotgun Lipidomics: Electrospray Ionization Mass Sectrometric Analysis And Qunatitation of Cellular Lipidomes Directly From Crude Extracts Of Biological Samples," authored by Xianlin Han and Richard W. Gross, published in Mass Spectrometry Reviews, Jun. 18, 2004. The foregoing articles by Han and Gross are hereby incorporated herein by reference.

In one embodiment, shotgun lipidomics can be carried out using all or any portion of the steps described above with regard to isotopically labeling samples of a cell population. In one embodiment, shotgun lipidomics can be carried out on a cell lysate without the need to use chromatography. The cell lysate can be whole cell lysate or a fraction of the whole cell lysate (e.g. extracted plasma membrane). Although shotgun lipidomics can be used to avoid the use of chromatography, chromatography may be used in combination with shotgun lipidomics if desired.

The mass spectrometry data can be used to identify the types and relative abundance of lipids in the sample. Lipidomic databases and algorithms that use mass sepctrometery data to identify specific lipids are known. Databases of lipids that can be used to identify the lipids in the sample include LIPID MAPS, Lipid Bank, CyberLipids, and LIPIDAT. The LIPID MAPS database also includes tandem mass spectrometry (MS/MS) fragment information for many lipid molecular species. Methods for performing mass spectrometry on lipids are disclosed in the following, which are hereby incorporated by reference: Hermansson M, Uphoff A, Kakela R, Somerharju P: Automated quantitative analysis of complex lipidomes by liquid chromatography/mass spectrometry. Anal Chem 2005, 77:2166-2175; Houjou T, Yamatani K, Imagawa M, Shimizu T, Taguchi R: A shotgun tandem mass spectrometric analysis of phospholipids with normal-phase and/or reverse-phase liquid chromatography/electrospray ionization mass spectrometry. Rapid Comm Mass Spectrom 2005, 19:654-666; Guan X L, He X, Ong W Y, Yeo W K, Shui G, Wenk M R: Non-targeted profiling of lipids during kainate-induced neuronal injury. FASEB J 2006, 20:1152-1161; Bijlsma S, Bobeldijk I, Verheij E R, Ramaker R, Kochhar S, Macdonald I A, vanOmmen B, Smilde A K: Large-scale human metabolomics studies: A strategy for data (pre-) processing and validation. Anal Chem 2006, 78:567-574; Ekroos K, Chernushevich I V, Simons K, Shevchenko A: Quantitative profiling of phospholipids by multiple precursor ion scanning on a hybrid quadrupole time-of-flight mass spectrometer. Anal Chem 2002, 74:941-9949; Han X, Gross R W: Global analyses of cellular lipidomes directly from crude extracts of biological samples by ESI mass spectrometry: a bridge to lipidomics. J Lipid Res 2003, 44:1071-1079.

The relative abundance of the lipids in the first and second samples is determined using the mass spectrometry data. The mass spectrometer provides separate peaks for the same type of lipid molecules in the first sample and the second sample. The mass spectrometry data yields a peak pair for a given type of lipid molecule due to the isotopic labeling in one of the two samples. Thus, one peak of a peak pair corresponds to a lipid from one sample and the other peak of the peak pair corresponds to the same lipid in the other sample. The isotopic labeling of the samples allows the mass spectrometer to distinguish between the identical lipid molecules that originate from the first sample compared to the second sample, despite the fact that the lipids from both samples are combined and processed together.

The peak intensities are computed and used to measure the relative amounts of lipids of interest in the first and second samples. The peak intensities are calculated in a conventional manner.

Figure 2:
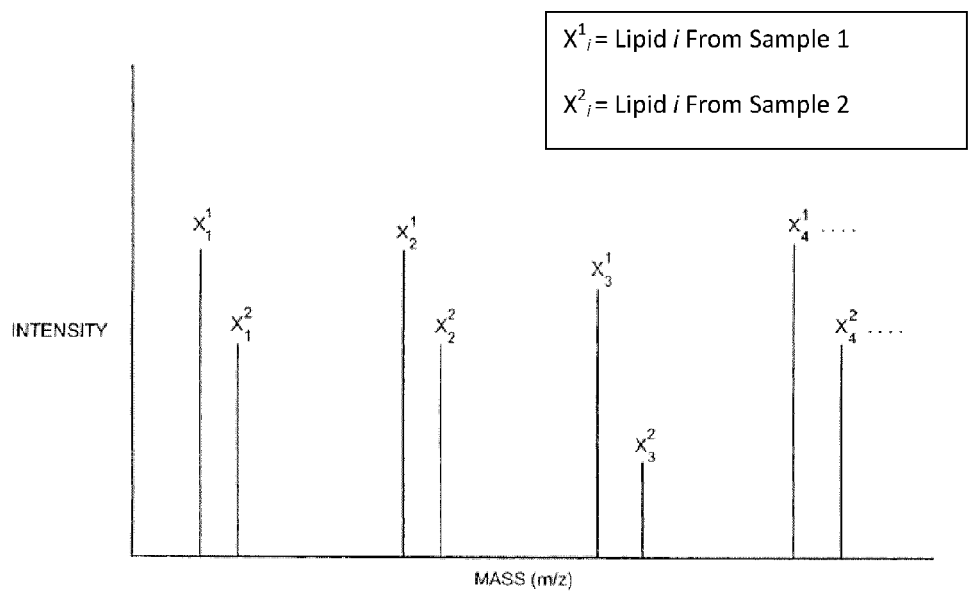
FIG. 2 shows mass spectroscopy peak pairs of a hypothetical example of lipids analyzed using the method described in FIG. 1.

The ratios of the peak intensities of each pair of peaks are a measure of the relative amount of a particular lipid in each sample. FIG. 2 is an example mass spectrum of four different lipids from a single combined sample resulting from a hypothetical experiment conducted in accordance with the method of FIG. 1. Because of the difference between the masses of the lipids from samples grown in the non-labeled medium and those grown in the labeled, isotopically enriched medium, the results of the mass spectroscopy will generally be a plurality of pairs of closely spaced peaks, each peak being at a different m/z ratio. Since the enriched isotope is typically heavier than the most abundant naturally occurring isotope, the peak at the higher m/z ratio is generally indicative of the relative abundance of the lipid from a labeled lipid grown in the medium enriched in one or more isotopes. The peak at the lower m/z ratio is generally indicative of the relative abundance of the peptide from an unlabeled lipid in the medium containing a normal abundance of isotopes.

Table I, below, lists four ratios of the peak intensities of non-isotopically labeled lipids of Sample 1 and isotopically labeled lipids of Sample 2 ($X_i^1/X_i^2$) based on the example mass spectrum of FIG. 2.

TABLE 1

| Lipid | Intensity Ratio |
| --- | --- |
| 1 | 0.70 ± 0.02 |
| 2 | 0.69 ± 0.02 |
| 3 | 0.30 ± 0.02 |
| 4 | 0.71 ± 0.02 |

Since the number of cells in one sample may differ from the number of cells in the other sample, for any given pair of peaks, the intensity of a peak corresponding to a lipid from one sample may differ from the intensity of the peak corresponding to the same sample from the other cell pool. The ratios between most of the pairs of peaks (which are indicative of samples derived from lipids unaffected by a given treatment or stimulus), will generally be the same. A deviation from the regularly observed ratio indicates a difference in the relative quantity of a peptide, and hence a lipid, between the two samples which may be caused by the modulation to which one of the samples has been subjected. The difference can be quantified in accordance with the present invention.

Because the samples are a combined sample during mass spectrometry, other sources of differences in the intensities of the peaks, such as variations in the extraction efficiency of a particular protein from the sample, the subsequent extraction efficiency of a lipid during liquid chromatography, the ionization efficiency of the mass spectrometer for a particular lipid, and/or other such factors, affect both samples equally. These factors should not, therefore, affect the observed ratios. Analyzing the ratio of the pair of peaks compensates for differences in mass intensities resulting from differences in the ionization efficiency of the mass spectrometer for a particular lipid. Isotopically labeling one of the two samples and observing the ratio between the peaks of the isotopically labeled and non-isotopically labeled lipids also compensates for differential effects between the samples themselves, such as the presence of a different number of cells in each, providing an internal normalization between the samples.

The ratios of the intensities of the peaks in the hypothetical spectrum shown in FIG. 2 is about 0.70, except for lipid number 3, whose ratio is about 0.30. This indicates that the relative amount of the lipid corresponding to lipid 3 in the first and second samples is different than the relative amounts of the lipids corresponding to lipids 1, 2 and 4. This suggests that the modulation affects the cellular production of the lipid and/or its concentration within a particular component of the cell (e.g., the cell membrane). In a full data set, there may be other pairs of peaks having ratios of about 0.30, corresponding to a fragment of the same lipid or another lipid or lipid fragment that is modulated in the same way as lipid 3. Analysis of the plurality of peaks having a ratio of about 0.30 would enable an identification of the lipid using a database and/or algorithms as discussed above.

The percentage difference between the regularly observed ratio of the peak intensities of the lipids from lipids 1, 2, and 4 compared to the observed ratio of the peak intensities of lipid 3 is caused by the modification of Sample 2. This quantitative change caused by the modification may give insight into the mechanism by which the modification affects cells in the sample.

The method of the invention can also be extended to comparing the effects of two or more modulations by preparing three or more samples wherein at least one isotope in each sample is different from the other samples.

The ability to avoid introducing variation during processing of the sample and to normalize variations inherent in the samples provides very high sensitivity for detecting small changes in the biological sample that are difficult, if not impossible, to detect using known techniques for identifying differences in lipids in two biological samples.

In addition, modifications, such as phosphorylation, glycosylation or acylation, at specific sites on individual lipids may be detected and quantified through mass spectroscopy in accordance with the present invention.

Additional Embodiments

A. Stable Isotope Labeled Proteins

In one embodiment of the invention, the methods using stable isotope labeled lipids in cell culture described above can be carried out in combination with a method using stable isotope labeled amino acids in cell culture in which cell modulation affects the expression of one or more proteins in a cell and the change in expression is observed using isotopically labeled amino acids and mass spectrometry. In this embodiment the isotope used in the media is typically a labeled amino acid such as, but not limited to labeled lysine and/or argenine. Examples of methods and techniques that can utilize stable isotope labeled lipids in cell culture are described in U.S. Pat. Nos. 6,391,649 and 6,653,076 to Chait and Franza, respectively, and an article authored by M. Mann, entitled "Is Proteomics the New Genomics?," published in Cell, Volume 130, Issue 3, Pages 395-398, all of which are hereby incorporated herein by reference.

B. Detecting Biological Components Associated with a Membrane Protein

The present invention also includes a method for identifying a biological component associated with a membrane protein using mass spectrometry. In this embodiment, a biological component of a cell (e.g., lipid, protein, nucleic acid, hormone, small organic molecule, cofactor, and/or carbohydrate, etc.) is identified as associated with a membrane protein in a biomembrane. To identify the association of the biological component with a biomembrane protein of interest, the biological component is isotopically labeled in one of two samples of a cell population and the biomembrane protein of one of the samples is modulated in some manner. The biomembrane is then isolated and analyzed using mass spec to detect a change in the biological component that correlates with the change in the membrane protein.

The present invention can be carried out using steps similar to those described above for identifying labeled lipids. In this embodiment, a membrane protein is modulated and the biomembranes are isolated. The extraction of the biomembrane includes the biological component and the biological component is not necessarily a lipid. The biological component can be a lipid, protein, nucleic acid, small molecule, or any other biological component that can be labeled with a stable isotope.

The biological component is isotopically labeled using a biological component precursor. The biological component precursor can be any compound that can be included in a media and utilized by the propagating cells to make a biological component. Examples of biological component precursors suitable for isotopically labeling lipids, proteins, carbohydrates, cofactors, derivatives of these and the like, include isotopically labeled glucose, amino acids, nucleic acid bases, and combinations of these.

In addition to labeling a biological component of one of the cell populations, the sample preparation also includes isolating the biomembrane that includes the biological component and/or the membrane protein. The sample preparation can include separating the target biomembrane from the cytosol and/or another type of biomembrane. Suitable techniques for isolating the biomembranes include the extracting and/or separating techniques described above with regard to lipids. However, in this embodiment, the extraction technique is selected such that the biological component remains associated with the membrane protein and/or the biomembrane at least during the separation of the biomembrane from the cytosol. In addition, the isolation technique can be selected according to the biological component. For example, where the biological component is a protein, protein isolation, extraction, purification, and separation techniques can be used.

Following isolation of the biomembranes (i.e., separating the biomembranes from at least a portion of the cytosol), the biomembranes can be further processed. In one embodiment, membrane associated biological components can be extracted from the biomembrane. Because the biomembrane associated biological components are extracted from the biomembrane after removing the cytosolic fraction, a distinction can be made between the portion of a particular biological component that was associated with the biomembrane and the portion of the same particular biological component that was in the cytosol. This allows changes in the biomembrane to be detected that would not otherwise be detectable given the background noise and/or changes that occur with the biological component in the cytosolic portion.

In some cases, a particular biological component may be associated with two different types of biomembranes (e.g., the cell membrane and the rough ER). In one embodiment of the invention, the procedure described above using the biological component includes separating the two types of biomembranes and extracting the biological component from the biomembrane of interest after the two biomembranes are separated. Examples of suitable techniques for separating biomembranes are described above.

Separating two or more types of biomembranes allows for observing changes in the biomembrane of individual organelle or the cell membrane. This technique can be highly advantageous where the individual changes in a biological component of interest associated with a biomembrane would otherwise be masked by changes occurring in all the biomembranes in a cell. (e.g., where lipid is transferred from one biomembrane to another with the membrane protein, the overall concentration of lipid in the cell does not change). Thus, isolating individual biomembranes can be particularly useful for studying the association of biological components with membrane proteins, since membrane proteins are found in membranes. For example, a membrane protein can be over expressed or under expressed and then the biomembrane where the membrane protein resides can be isolated and the biomembrane analyzed for increases or decreases in a biological component, thereby identifying the association between the biological component and the membrane protein.

An example of a method that can be used according to this embodiment includes:
(i) culturing a first sample of a cell population in a first medium, the first medium including a biological component precursor having a first abundance of at least one isotope;
(ii) culturing a second sample of a cell population in a second medium, the second medium including the biological component precursor with a second and different abundance of the at least one isotope, wherein the biological component precursor in each of the samples is incorporated into a biological component within the respective sample;
(iii) modulating a membrane protein in one of the samples of the cell population, wherein the modulation: creates a difference in the membrane protein of the one sample compared to the other sample; and creates a difference in the biological component of the one sample compared to the other sample;
(iv) isolating at least a portion of the biomembranes from the first and second samples by separating the biomembranes from the cytosol, wherein the biomembranes include the biological component associated therewith;
(v) combining at least a portion of the biomembranes from the first sample with a portion of the biomembranes from the second sample to form a combined sample, the combined sample including the biological component from the first sample and the second sample;
(vi) subjecting the combined sample to mass-spectrometry; and
(vii) determining the relative abundance of the biological component in the biomembranes of the first sample compared to the biomembranes of the second sample, thereby identifying a biological component that is modified in response to the modification of the membrane protein.

In step (iii) the modification to the membrane protein can be any modification, including over- or under-expression of the membrane protein, or a structural modification such as phosphorylation. The resulting change in the biological component can be any change in the biological component such as, but not limited to, an increase or a decrease in concentration of the biological component within the biological membrane or a structural modification to the biological component (e.g., phosphorylation).

In step (vi), any mass-spectrometer can be used that is compatible with the combined sample and the particular biological component of interest. The type of mass-spectrometer used will depend on the particular biological component of interest. It is known how to collect mass spectrometry data for biological components such as, but not limited to, proteins, lipids, nucleic acids, and small organic molecules.

The relative abundance of the biological component in the samples can be determined by using the ratios of the intensities of the peak pairs as described above with respect to lipids. However, the ratios being calculated are for the biological component, which may or may not be a lipid.

The use of mass spectrometry to identify an association of a biological component with a membrane protein in a biomembrane is highly advantageous. Using mass spectrometry in combination with a labeled biological component allows biological components to be identified that have relatively low concentrations in the biomembrane. By isolating the biomembrane a significant portion of the unimportant changes that occur from modulating the membrane protein (e.g., cellular effects from over expressing a protein) can be eliminated, thereby allowing detection of very small changes in the biomembrane. For example, removing the cytosol and endoplasmic reticulum from the sample can remove the majority of proteins and other cellular components that change in concentration when a protein is over-expressed, thereby eliminating a significant portion of the "noise" in the mass spectrometry data and allowing subtle changes in the biomembrane to be detected. The detection of subtle changes in a biological component of the biomembrane then allows these changes to be associated with the modulated membrane protein and the determination that the biomembrane and the biological component are functionally related in the membrane.

What is claimed is:
1. A method for determining the relative abundance of a lipid of interest, comprising:
(i) culturing a first sample of a cell population in a first medium, the first medium including a lipid precursor having a first abundance of at least one isotope;
(ii) culturing a second sample of the cell population in a second medium, the second medium including the lipid precursor with a second and different abundance of the at least one isotope,
wherein the lipid precursor in each of the samples is incorporated into a biological lipid within the respective samples;
(iii) modulating one of the samples of the cell population;
(iv) isolating one or more lipids from each of the first and second samples, the lipids from each of the samples including the biological lipid;
(v) combining at least a portion of the first sample and a portion of the second sample to form a combined sample, the combined sample comprising the biological lipids from each of the samples;

(vi) subjecting the isolated lipids in the combined sample to mass-spectrometry; and (vii) determining the relative abundance of a lipid of interest in the first sample compared to the second sample.

2. The method as in claim 1, wherein the mass spectrometry technique in step (vi) is a shotgun lipidomics mass spectrometry technique.

3. The method as in claim 1, wherein the isolation in step (iv) comprises separating at least one type of biomembrane from another type of biomembrane.

4. The method as in claim 1, wherein the isolation in step (iv) comprises isolating the plasma membrane of the cells.

5. The method as in claim 1, where the isolation in step (iv) includes extracting and/or separating lipids using a technique selected from the group consisting of cell lysis, low speed centrifugation, high speed centrifugation, ultra centrifugation, density gradient centrifugation, lipid extraction, high performance liquid chromatography, liquid chromatography, electrophoresis, affinity chromatography and combinations thereof.

6. The method as in claim 1, wherein the lipid precursor is an isotopically labeled glycerol, serine, cholesterol, or combination thereof.

7. The method as in claim 1, wherein the modulation of step (iii) creates a modification in the lipid of interest in one sample compared to the other sample, where the modification comprises a chemical structure modification of the lipid of interest, a difference in the rate of synthesis of the lipid of interest, a difference in the rate of degradation of the lipid of interest, a difference in a concentration of the lipid of interest, and/or a difference in the location of the lipid of interest within the cell population.

8. The method as in claim 7, wherein the lipid of interest increases or decreases in concentration within a biomembrane.

9. The method as in claim 1, wherein the modulation of the sample comprises exposing the sample to a cellular change, a chemical change, a genetic change, an environmental change, or a combination thereof.

10. The Mil method as in claim 1, wherein the modulation of the sample comprises exposing the sample to a genetic change, wherein the genetic change comprises over-expressing or under-expressing a protein in the sample.

11. The method as in claim 10, wherein the over-expressed or under-expressed protein includes an integral membrane protein.

12. The method as in claim 1, wherein one of the first medium or the second medium includes an amino acid, the amino acid having a different abundance of isotope in the first medium compared to the second medium, the method further comprising (viii) extracting a mixture of proteins from the combined sample; (ix) subjecting the mixture of proteins to mass spectrometry; and (x) determining the relative abundance of a protein of interest in the first sample compared to the second sample.

* * * * *